United States Patent [19]

Belyaev et al.

[11] 4,067,923
[45] Jan. 10, 1978

[54] PROCESS FOR PRODUCING ISOPRENE

[76] Inventors: Vladimir Alexandrovich Belyaev, prospekt Oktyabrya, 41, kv. 20, Yaroslavl; Vladimir Leontievich Rudkovsky, ulitsa Karbysheva, 17, kv. 21, Volzhsky Volgogradskoi Oblasti, both of U.S.S.R.

[21] Appl. No.: 651,142

[22] Filed: Jan. 21, 1976

[51] Int. Cl.² .............................................. C07C 11/18
[52] U.S. Cl. ..................................................... 260/681
[58] Field of Search ........................................ 260/681

[56] References Cited

U.S. PATENT DOCUMENTS

| 2,350,485 | 6/1944 | Arundale et al. | 260/681 |
| 2,381,148 | 8/1945 | Weizmann | 260/681 |
| 2,993,940 | 7/1961 | Oldnam | 260/681 |
| 3,536,744 | 10/1970 | Itoi et al. | 260/681 |

Primary Examiner—C. Davis
Attorney, Agent, or Firm—Haseltine, Lake & Waters

[57] ABSTRACT

A process for producing isoprene comprising reacting formaldehyde and isobutylene or trimethylcarbinol or with a mixture of isobutylene with trimethylcarbinol in a liquid phase upon heating to a temperature of about 200° C in the presence of a catalyst, viz. sulphamic acid or an aromatic ammonium compound containing a sulpho group in ortho-, meta- or para-position and having the formula:

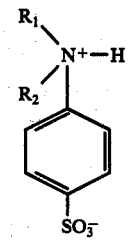

wherein $R_1$ and $R_2$ are hydrogen, an alkyl, aryl, alkylaryl, aralkyl;

hydrogen atoms in the benzene ring may be substituted for an alkyl, halide or sulpho group; or in the presence of a catalyst such as an ammonium condensed compound of the naphthalene series containing a sulpho group and having the formula:

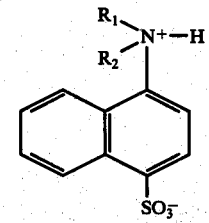

wherein $R_1$ and $R_2$ are hydrogen, an alkyl, aryl, alkylaryl, aralkyl; and as the calalyst use is made of reaction products of said ammonium compounds with formaldehyde, followed by isolation of the desired product.

Isoprene produced by the process according to the present invention is useful in the production of various rubbers.

16 Claims, No Drawings

PROCESS FOR PRODUCING ISOPRENE

The present invention relates to the art of petrochemistry and, more specifically, to a process for producing isoprene.

Isoprene is a principal monomer in the production of various rubbers. Isoprene is mainly used in the synthesis of stereospecific polyisoprene rubber with the properties approaching those of natural rubber.

Known in the art is a two-stage process for producing isoprene from isobutylene and formaldehyde with several embodiments of the process technology.

At the first stage of the process 4,4-dimethyldioxane-1,3 is produced from isobutylene and formaldehyde in a liquid phase at a temperature within the range of from 85° to 95° C and at the molar ratio between formaldehyde and isobutylene equal to 2:1, using sulphuric acid as a catalyst. Formaldehyde conversion is 85-90%. Yield of 4,4-dimethyldioxane-1,3 is as high as 80 mol.% for the reacted formaldehyde. At the second stage 4,4-dimethyldioxane-1,3 is transformed to isoprene using a solid heterogeneous catalyst at a temperature within the range of from 370° to 390° C. Total conversion of 4,4-dimethyldioxane-1,3 is 90-95%. Yield of isoprene is 80-85 mol.% for the reacted 4,4-dimethyldioxane-1,3.

This prior art process has a disadvantage residing in a high energy consumption in the process of decomposition of 4,4-dimethyldioxane-1,3 and in the necessity of recuperating the formaldehyde resulting from the decomposition of 4,4-dimethyldioxane-1,3. The latter operation of formaldehyde recuperation causes some difficulties and is accompanied by losses of rather expensive raw materials.

The difficulties encountered in the recuperation of formaldehyde may be overcome by the use of 3-methylbutanediol-1,3 as an intermediate product in the production of isoprene.

The process for producing isoprene from formaldehyde and isobutylene via 3-methylbutanediol-1,3 is also known in the art. Unlike in the above-described process, the first stage is effected using a diluted solution of formaldehyde (weight ratio $H_2O:CH_2O=20:1$) and an excessive amount of isobutylene. The yield of 3-methylbutanediol-1,3 is 55-64 mol.% for the converted formaldehyde with the conversion of formaldehyde equal to 96%. In the second stage the resulting 3-methylbutanediol-1,3 is subjected to dehydration. This heterogeneous dehydration of 3-methylbutanediol-1,3 is performed under rather mold conditions, i.e. at a temperature within the range of from 250° to 300° C; the yield of isoprene is 80-85 mol.% based on the decomposed 3-methylbutanediol-1,3; in the homogeneous dehydration in the presence of 3-7% solution (by weight) of sulphuric acid at the temperature of 120° C. The yield of isoprene is as high as 82 mol.% as calculated for the reacted 3-methylbutanediol-1,3. However, a commercial process involving the stage of synthesis of 3-methylbutanediol-1,3 has not been developed, since the problem of economically efficient recovery of 3-methylbutanediol-1,3 from diluted aqueous solution was not solved and decomposition of the resulting mixture on a solid catalyst was impossible to perform without preliminary separation. Homogeneous dehydration of 3-methylbutanediol-1,3 in the presence of sulphuric acid constitutes a serious problem because of the equipment corrosion.

Also known in the art is a process for producing isoprene by reacting formaldehyde with isobutylene in the presence of water or an aqueous solution of trimethylcarbinol in a liquid phase at a temperature within the range of from 110° to 180° C using, as catalysts, inorganic compounds, acidic substances under the conditions of said reaction, chlorides, sulphates or phosphates of metals pertaining to I-VIII Groups of the periodic system, a cation-exchange resin. Molar ratio between isobutylene and formaldehyde is varied within the range of from 1:1 to 10:1 respectively. Yield of isoprene as calculated for formaldehyde is about 70-84 mol.%.

The catalysts as employed in said prior art process are corrosion-active compounds, wherefore commercial implementation of the process is restricted. Commercial equipment may suffer from decomposition of iron salts and formation of friable deposits of metal hydroxides during neutralization of the aqueous layer with alkalis.

The majority of the prior art catalysts reacts with unsaturated hydrocarbons taking part in the synthesis or evolves compounds reacting therewith. Thus, when hydrochloric acid is employed as well as chlorides of iron, chromium, aluminium, cobalt and the like, there occurs a reaction of the salt hydrolysis and hydrochlorination of unsaturated products; in the case of using sulphuric acid and sulphates of the above-mentioned elements, alkylsulphuric acids are formed; cation-exchange resins are hydrolyzed at the reaction temperature with liberation of sulphuric acid which forms said alkylsulphuric acids. Hydrohalides of the unsaturated compounds and the alkylsulphuric acids ae not completely destroyed upon enutralization and are further hydrolysed in separation columns during subsequent processing of the reaction mass with the evolution of acidic fcorrosion-active compounds. This reults in a complicated procedure of isolation of the desired products and necessitates the use of the process equipment made of acid-resistant materials in all the stages of the technological process; furthermore, it causes an unreasonably high catalyst consumption.

It is the principal object of the present invention to simplify the process technology.

It is another object of the present invention to increase the desired product yield.

The principal and other objects are accomplished by that in a process for producing isoprene, wherein formaldehyde is reacted with isobutylene or trimethylcarbinol or with a mixture of isobutylene and trimethylcarbinol in a liquid phase upon heating to a temperature of about 200° C, in accordance with the present invention, said reaction is conducted in the presence of a catalyst, viz. sulphamic acid or an aromatic ammonium compound containing a sulpho group in ortho-, meta- or para-position and correspondsing to the formula:

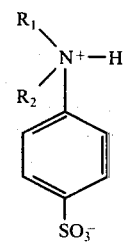

wherein R₁ and R₂ are hydrogen, an alkyl, aryl, alkylaryl, aralkyl;
hydrogen atoms in the benzene ring may be substituted for an alkyl, halide or sulpho group; or in the presence of a catalyst such as a condensed ammonium compound of the naphthalene series containing a sulpho group and corresponding to the formula:

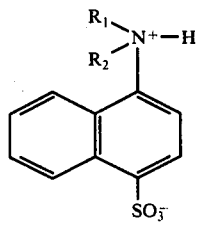

wherein R₁ and R₂ are selected from the group consisting of hydrogen, an alkyl, aryl, alkylaryl, aralkyl; or a reaction product of said ammonium compounds with formaldehyde, followed by isolation of the desired products.

Isoprene synthesis is conducted at a temperature within the range of from 7° to 200° C.

It is desirable to perform the process in two successive temperature ranges of from 70° to 130° and 160° to 200° C respectively, since during the lasting operation under the same temperature conditions ensuring production of isoprene the reactor becomes clogged with a solid product containing polyformaldehyde.

It is advisable to use, as the catalysts, sulphanilic acid, methanilic acid, orthanilic acid; aniline-3,5-disulphoric acid, 2,5-dichloroaniline-4-sulphonic acid, 1,4-toluidine-3-sulphonic acid, monobenzylsulphanilic acid, dibenzylsulphanilic acid or 1-naphthylamine-4-sulphonic acid and reaction products of sulphanilic acid with formaldehyde or methanilic acid with formaldehyde, or sulphamic acid with formaldehyde. or 1-naphthylamine-4-sulphonic acid with formaldehyde. The catalysts of the present invention contain amino and sulpho groups thus making it possible to reduce corrosion activity of the reaction mass; furthermore, they are non-volatile, thermally and hydrolytically stable compounds and do not react with unsaturated compounds.

The present invention is embodied in the following manner Into the first reactor of the reaction unit consisting of two series-connected reactors the starting products are charged: 40–35 wt.% of an aqueous formaldehyde solution, isobutylene and a catalyst. The reaction products are discharged from the second reactor.

Instead of isobutylene use may be made of trimethylcarbinol.

In the process according to the present invention isoprene is produced using various molar ratios between formaldehyde and isobutylene. It is preferable to maintain a molar ratio between formaldehyde and isobutylene within the range of from 1:13 to 1:6 respectively. Lesser molar ratio results in incomplete conversion of formaldehyde. Further increase of the upper limit of said ratio (over 1:6) does not give any increase in the yield of isoprene and, hence, is inexpedient. It is preferable to conduct the reaction in the presence of a mixture of trimethylcarbinol and isobutylene. In this case a molar ratio between formaldehyde and (isobutylene + trimethylcarbinol) is maintained within the range of from 1:3 to 1:6.

In accordance with the present invention, the process is performed in two successive temperature intervals: in the first reactor is maintained at a temperature within the range of from 70° to 130° C, while in the second the temperature is within the range of from 160° to 200° C. Heating of the reactors in effected by means of a heat-transfer medium supplied into the heating jackets of the reactors. Such a mode of the process is selected to ensure stable operation conditions of commercial plants, since lasting operation under the same temperature conditions necessary for the production of isoprene may result in clogging of the equipment with a solid product containing polyformaldehyde. At a temperature below 70° C, the rate of formaldehyde conversion becomes too low, whereby the desired product yield is substantially reduced. Temperatures below 160° C result in a reduced yield of the desired product due to incomplete conversion of the intermediate reaction products to isoprene; temperatures above 200° C also result in a reduced yield of the desired product due to increased rates of the side reactions.

In the process of the present invention use is made, as the catalyst, of sulphamic acid, sulphanilic acid, methanilic acid, orthanilic acid as well as aniline-3,5-disulphonic acid, 2,5-dichloroaniline-4-sulphonic acid, 1,4-toluidine-3-sulphonic acid, monobenzylsulphanilic acid, dibenzylsulphanilic acid or 1-naphthylamine-4-sulphonic acid which are dry crystalline products.

Condensation of isobutylene with formaldehyde is effected at an elevated pressure and temperature, wherefore dosage of the crystalline products in the continuous operation reactors is hindered. For commercial plants it is most convenient to employ, as the catalysts, reaction products of the above-mentioned organic and inorganic ammonium compounds containing a sulpho group with formaldehyde. These catalysts are obtained by mixing one of the above-mentioned compounds with an aqueous solution of formaldehyde at a temperature of from 10° to 60° C. Water content in the reaction mass ranges from 90 to 20% by weigh; ammonium compound containing a sulpho group amounts to 5–40% by weight; formaldehyde content is 5 to 40% by weight.

To produce isoprene by the process according to the present invention, the catalyst is used in rather small amounts, i.e. of the order of from 0.01 to 0.1% by weight of the reaction mixture which is 50 times as less as in the prior art process.

The use of a catalyst containing amino and sulpho groups makes it possible to substantially reduce its corrosion activity and simplify the proess technology, since the catalysts of the present invention are non-volatile, thermally and hydrolytically stable compounds which do not react with unsaturated compound. Furthermore, presence of amino group in the catalyst molecule imparts thereto properties of an inhibitor of isoprene thermopolymerization and isoprene-isobutylene copolymerization as well as properties of a surfactant ensuring letter intermixing of organic and aqueous phases.

For a better understanding of the present invention, some specific examples illustrating production of isoprene are given hereinbelow.

EXAMPLE 1

A metallic ampoule provided with a heating jacket and a thermocouple is charged with 8.3 g of a 36% (by weight) aqueous solution of formaldehyde containing 6.0 wt.% of methanol, 25.2 g of a 88% (by weight) aqueous solution of trimethylcarbinol and 0.05 g of sulphanilic acid. The ampoule is hermetically sealed and charged, through a valve, with 16.8 g of isobutylene (molar ratio formaldehyde: trimethylcarbinol: isobutylene is 1:3:3). The sealed ampoule is placed into a shaker; a heat-transfer medium is supplied into the heating jacket and the ampoule contents are heated to 130° C for 5–7 minutes. Reaction time at 130° C is 30 minutes. Then the reaction mass is heated to 180° C for 5–7 minutes and maintained at this temperature for 45 minutes. On completion of the reaction the ampoule is cooled to 15° C for 5 minutes. The reaction mass consisting of two layers is discharged into cooled vessels and weighed. Composition of the organic and aqueous layers is determined chromatographically. Formaldehyde converion is 100%.

Yield of isoprene is 74.0 mol.% as calculated for formaldehyde. By-products formed in the synthesis are recycled, thus inhibiting the formation of additional amounts of these by-products.

EXAMPLE 2

The procedure of Example 1 is repeated except that as the catalyst use is made of 0.05 g of methanilic acid.
Formaldehyde conversion is 100%.
Isoprene yield is 72.0 mol.% as calculated for formaldehyde.

EXAMPLE 3

Experiment procedure, conditions and charging operation of Example 1 are repeated, except that as the catalyst use is made of 0.05 g of orthanilic acid.
Formaldehyde conversion is 100%.
Isoprene yield is 69.0 mol.% as calculated for formaldehyde.

EXAMPLE 4

Experiment procedure, condition and charging operation of Example 1 are repeated, except that as the catalyst use is made of 0.028 g of sulphamic acid.
Formaldehyde conversion is 100%.
Isoprene yield is 68.0 mol.% as calculated for formaldehyde.

EXAMPLE 5

Experiment procedure, conditions and charging operation of Example 1 are repeated, except that as the catalyt use is made of 0.045 g of 1-naphthylamine-4-sulphonic acid.
Formaldehyde conversion is 99%.
Isoprene yield is 59.0 mol.% as calculated for the reacted formaldehyde.

EXAMPLE 6

Experiment procedure, condition and charging operation of Example 1 are repeated, except that as the catalyst use is made of 0.05 g of monobenzylsulphanilic acid.
Formaldehyde converion is 99.5%.
Isoprene yield is 58 mol.% a calculated for the reacted formaldehyde.

EXAMPLE 7

Experiment procedure, conditions and charging operation of Example 1 are repeated, except that as the catalyst use is made of 0.048 g of dibenzylsulphanilic acid.
Formaldehyde conversion is 98.5%.
Isoprene yield is 57.5 mol.% as calculated for the reacted formaldehyde.

EXAMPLE 8

Experiment procedure, conditions and charging operation of Example 1 are repeated, except that as the catalyst use is made of 0.03 g of 2,5-dichloroaniline-4-sulphonic acid.
Formaldehyde conversion is 99.6%.
Isoprene yield is 56.0 mol.% as calculated for the reacted formaldehyde.

EXAMPLE 9

Experiment procedure, conditions and charging operation of Example 1 are repeated, except that as the catalyst use is made of 0.045 g of 1,4-toluidine-3-sulphonic acid.
Formaldehyde conversion is 99.0%.
Isoprene yield is 60 mol.% as calculated for the reacted formaldehyde.

EXAMPLE 10

Experiment procedure, conditions and charging operation of Example 1 are repeated, except that as the catalyst use is made of 0.035 g of aniline-3,5-disulphonic acid.
Formaldehyde conversion is 99.8%.
Isoprene yield is 69.0 mol.% as calculated for the reacted formaldehyde.

EXAMPLE 11

Experiment conditions and procedure of Example 1 are repeated. Into a metallic ampoule 12.91 g of a 36% (by weight) of an aqueous solution of formaldehyde containing 6.0% by weight of methanol; 40.16 g of a 88.0% (by weight) aqueous solution of trimethylcarbinol and 0.053 g of sulphanilic acid are charged. Molar ratio between formaldehyde and trimethylcarbinol is equal to 1:3.
Formaldehyde conversion is 100%.
Isoprene yield is 70.0 mol.% as calculated for formaldehyde.

EXAMPLE 12

Experiment conditions, procedure and charging operation are as in the foregoing Example 11, except that as the catalyst use is made of 0.053 g of methanilic acid.
Formadehyde conversion is 100%.
Isoprene yield is 69.0 mol.% as calculated for formaldehyde.

EXAMPLE 13

Experiment procedure and conditions are as in Example 1. Into a metallic ampoule 8.3 g of a 36% (by weight) aqueous solution of formaldehyde containing 6.0% by weight of methanol, 33.6 g of isobutylene and 0.042 g of sulphanilic acid are charged. Molar ratio between formaldehyde and isobutylene is equal to 1:6.
Formaldehyde conversion is 100%.
Isoprene yield is 65.0 mol.% as calculated for formaldehyde.

EXAMPLE 14

Experiment procedure, conditions and charging operation are as in the foregoing Example 13, except that as the catalyst use is made of 0.021 g of sulphamic acid.
Formaldehyde conversion is 99.5%.

Isoprene yield is 62.0 mol.% as calculated for the reacted formaldehyde.

EXAMPLE 15

Experimental procedure and charging operation are as in the foregoing Example 1, except that at the beginning the ampoule contents are heated to 70° C and then to 170° C. Reaction time at 70° C is 180 minutes, that at 170° C is 45 minutes.

Formaldehyde conversion is 100%.

Isoprene yield is 64.0 mol.% as calculated for formaldehyde.

EXAMPLE 16

Experiment procedure and charging operation are as in Example 1, except that the temperature conditions of the reaction are different, i.e. at the beginning the ampoule contents are heated to 110° C, then to 160° C. Reaction time at 110° C is 30 minutes; that at 160° C is 90 minutes.

Formaldehyde conversion is 100%.

Isoprene yield is 69.0 mol.% as calculated for formaldehyde.

EXAMPLE 17

Preparation of the reaction product of sulphanilic acid with formaldehyde.

Into a glass flask provided with a stirrer there are successively charged 15 g of a 36% by weight aqueous solution of formaldehyde containing 4.0% (by weight) of methanol, 20.9 g of water and 15 g of sulphanilic acid.

The reaction mass is stirred at room temperature for one hour and during this period the sulphanilic acid is completely dissolved. Upon storage for lasting periods under normal conditions (one month) no change of the catalytic activity or physical condition of the thus-prepared solution are observed.

Similar result are obtained for orthanilic acid, methanilic acid, sulphamic acid, 1-naphthylamine-4-sulphonic acid, 2,5-dichloroaniline-4-sulphonic acid, 1,4-toluidine-3-sulphonic acid and other above-mentioned compounds of ammonium.

EXAMPLE 18

Production of isoprene on a continuous-operation laboratory unit.

A continuous-operation laboratory unit consists of 4 principal sections: metering section, reaction section, section of stratification of aqueous and organic layers and section of collecting the reaction products. Metering section, section of stratification and section of collecting the reaction products are made in a known manner. The reaction section consists of two series-connected reactors of the "pipe-in-pipe" type.

Heating of the reactors is effected by means of a heat-transfer medium. The starting products are supplied into the bottom portion of the first reactor. From the top portion of the second reactor the reaction product are delivered to the stratification section. Fed into the reaction section for a period of 8 hours are 1,188 g of isobutylene; 406 g of a 36.0% (by weight) aqueous solution of formaldehyde containing 6.0% by weight of methanol; 554 g of a 88.0% (by weight) aqueous solution of trimethylcarbinol (molar ratio formaldehyde:trimethylcarbinol:isobutylene is equal to 1:1.3:4.4) and 3.58 g of a reaction product of sulphanilic acid with formaldehyde (sulphanilic acid content is 30% by weight).

Temperature in the first reactor is 120° C; that in the second reactor is 180° C. Contact time in each of the reactors is 8 minutes. The reaction products become stratified and then are fed into the product collection section, wherefrom the organic and aqueous layers are dicharged into cooled vessels and weighed. Composition of the organic and aqueous layers is determined chromatographically.

Formaldehyde conversion is 100%.

Isoprene yield is 88.0 mol.% as calculated for formaldehyde.

EXAMPLE 19

Experiment procedure, conditions and charging opeeration are as in the foregoing Example 18, except that as the catalyst use is made of 2.86 g of a reaction product of methanilic acid with formaldehyde (methanilic acid content is 30% by weight).

Formaldehyde conversion is 100%.

Yield of isoprene is 86.0 mol.% as calculated for formaldehyde.

EXAMPLE 20

Experiment procedure, conditions and charging operation are as in the foregoing Example 18, except that as the catalyst use is made of 1.08 g of a reaction mass resulting from the interaction between sulphamic acid and formaldehyde (sulphamic acid content is 40% by weight).

Formaldehyde conversion is 100%.

Isoprene yield is 80.0 mol.% as calculated for formaldehyde.

EXAMPLE 21

Experiment procedure, conditions and charging operation are as in the foregoing Example 18, except that as the catalyst use is made of 2.86 g of a reaction product of orthanilic acid with formaldehyde (orthanilic acid content is 30% by weight).

Formaldehyde conversion is 100%.

Isoprene yield is 84.0 mol.% as calculated for formaldehyde.

EXAMPLE 22

Experiment procedure, conditions and charging operation are as in the foregoing Example 18, except that as the catalyst use is made of a reaction product of 1-naphthylamine-4-sulphonic acid with formaldehyde in the amount of 3.76 g (1-naphthylamine-4-sulphonic acid content is 40% by weight).

Formaldehyde conversion is 99.5%.

Isoprene yield is 72.0 mol.% as calculated for the reacted formaldehyde.

EXAMPLE 23

Experiment procedure, conditions and charging operation are as in the foregoing Example 18, except that as the catalyst use is made of 4.32 g of a reaction product of monobenzylsulphanilic acid with formaldehyde (monobenzylsulphanilic acid content is 25% by weight).

Formaldehyde conversion is 100%.

Isoprene yield is 70.0 mol.% as calculated for formaldehyde.

EXAMPLE 24

Experiment procedure, conditions and charging operation are as in the foregoing Example 18, except that as the catalyst use is made of 4.3 g of a reaction product of 2,5-dichloroaniline-4-sulphonic acid with formaldehyde (2,5-dichloroaniline-4-sulphonic acid content is 35% by weight).

Formaldehyde conversion is 99.6%.

Isoprene yield is 68.0 mol.% as calculated for formaldehyde.

EXAMPLE 25

Experiment procedure, conditions and charging operation are as in the foregoing Example 18, except that as the catalyst use is made of 2.87 g of a reaction product of 1,4-toluidine-3-sulphonic acid with formaldehyde (4-toluidine-3-sulphonic acid content is 15% by weight).

Formaldehyde conversion is 99.5%.

Isoprene yield is 80.0 mol.% as calculated for the reacted formaldehyde.

EXAMPLE 26

Experiment procedure, conditions and charging operation are as in the foregoing Example 18, except that as the catalyst use is made of 3.58 g of a reaction product of aniline-3,5-disulphonic acid with formaldehyde (aniline-3,5-disulphonic acid content is 30% by weight).

Formaldehyde conversion is 100%.

Isoprene yield is 83.0 mol.% as calculated for formaldehyde.

What is claimed is:

1. A process for producing isoprene comprising reacting formaldehyde with isobutylene and trimethylcarbinol in a liquid phase upon heating to a temperature of about 200° C in the presence of a catalyst selected from the group consisting of sulphamic acid, an aromatic ammonium compound containing a sulpho group in ortho- meta- or para-position and having the formula:

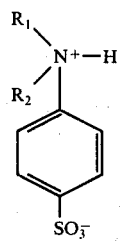

where $R_1$ and $R_2$ are selected from the group consisting of hydrogen, an alkyl, aryl, alkylaryl, aralkyl; hydrogen atoms in the benzene ring may be substituted by radicals of the group consisting of a methyl, halide, and sulpho group; as well as a catalyst selected from the group of ammonium condensed compounds of the naphthalene series containing a sulpho group and having the formula:

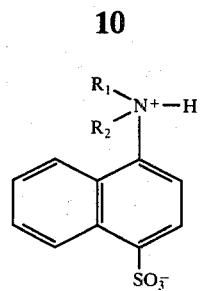

where $R_1$ and $R_2$ are selected from the group consisting of hydrogen, an alkyl, aryl, alkylaryl, aralkyl, and a reaction product of said ammonium compounds with formaldehyde, followed by isolation of the desired product.

2. A process as claimed in claim 1, wherein the reaction is performed in two successive temperature ranges, the first temperature range being from 70° to 130° C; the second temperature range being from 160° to 200° C.

3. A process as claimed in claim 1, wherein as the catalyst use is made of a compound selected from the group consisting of sulphanilic acid, methanilic acid, orthanilic acid, aninline-3,5-disulphonic acid, 2,5-dichloroaniline-4-sulphonic acid, 1,4-toluidine-3-sulphonic acid, monobenzylsulphanilic acid, dibenzylsulphanilic acid and 1-naphthylamine-4-sulphonic acid.

4. A process as claimed in claim 1, wherein the catalyst is a reaction product of formaldehyde with a compound selected from the group consisting of sulphanilic acid, sulphamic acid, methanilic acid, and 1-naphthylamine-4-sulphonic acid.

5. A process for producing isoprene comprising reacting formaldehyde with trimethylcarbinol in a liquid phase upon heating to a temperature of about 200° C in the presence of a catalyst selected from the group consisting of sulphamic acid, an aromatic ammonium compound containing a sulpho group in ortho-, meta or para-position and having the formula:

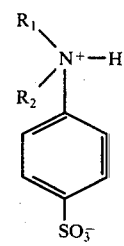

where $R_1$ and $R_2$ are selected from the group consisting of hydrogen, alkyl, aryl, alkylaryl, and aralkyl; hydrogen atoms in the benzene ring may be substituted by radicals of the group consisting of a methyl, halide, and a sulpho group; and a catalyst selected from the group consisting of ammonium condensed compound of the naphthalene series containing a sulpho group and having the formula:

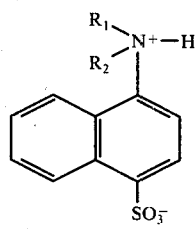

wherein $R_1$ and $R_2$ are selected from the group consisting of hydrogen, alkyl, aryl, alkylaryl, and aralkyl; and a reaction product of said ammonium compounds with formaldehyde, followed by isolation of the desired product.

6. A process as claimed in claim 5, wherein the reaction is performed in two successive temeprature ranges; the first temperature range being from 70° to 130° C; the second temperature range being from 160° to 200° C.

7. A process as claimed in claim 5, wherein as the catalyst use is made of compounds selected from the group consisting of sulphanilic acid, methanilic acid, orthanilic acid, aniline-3,5-disulphonic acid, 2,5-dichloroaniline-4-sulphonic acid, 1,4-toluidine-3-sulphonic acid, monobenzylsulphanilic acid, dibenzylsulphanilic acid and 1-naphthylamine-4-sulphonic acid.

8. A process claimed in claim 5, wherein as the catalyst is a reaction product of formaldehyde with compounds selected from the group consisting of sulphanilic acid, methanilic acid, sulphamic acid, and 1-naphthylamine-4-sulphonic acid.

9. A process for producing isoprene comprising reacting formaldehyde with isobutylene in a liquid phase upon heating to a tempterature of about 200° C in the presence of a catalyst selected from the group consisting of sulphamic acid, an aromatic ammonium compound containing a sulpho group in ortho-, meta- or para-position and having the formula:

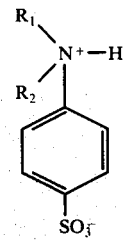

wherein $R_1$ and $R_2$ are selected from the group consisting of hydrogen, alkyl, aryl, alkylaryl, and aralkyl; hydrogen atoms in the benzene ring may be substituted by radicals of the group consisting of a methyl, halide, and sulpho group; a catalyst selected from the group consisting of ammonium condensed compound of the naphthalene series containing sulpho group and having the formula:

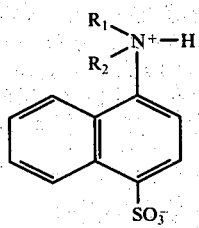

wherein $R_1$ and $R_2$ are selected from the group consisting of hydrogen, alkyl, aryl, alkylaryl, and aralkyl; and a reaction product of said ammonium compounds with formaldehyde, followed by isolation of the desired product.

10. A process as claimed in claim 9, wherein the reaction is performed in two successive temeprature ranges; the first temperature range being from 70° to 130° C; the second temperature range being from 160° to 200° C.

11. A process as claimed in claim 9, wherein as the catalyst use is made of a compound selected from the group consisting of sulphanilic acid, methanilic acid, orthanilic acid, aniline-3,5-disulphonic acid, 2,5-dichloroaniline-4-sulphonic acid, 1,4-toluidine-3-sulphonic acid, monobenzylsulphanilic acid, dibenzylsulphanilic acid and 1-naphthylamine-4-sulphonic acid.

12. A process as claimed in claim 9, wherein the catalyst is a reaction product of formaldehyde with a compound selected from the group consisting of sulphanilic acid, methanilic acid, sulphamic acid and b 1-naphthylamine-4-sulphonic acid.

13. A process for producing isoprene comprising reacting formaldehyde with a compound selected from the group consisting of isobutylene, trimethylcarbinol and mixtures thereof in a liquid phase upon heating to a temperature of about 200° C in the presence of a catalyst selected from the group consisting of sulphamic acid, an aromatic ammonium compound containing a sulpho group in ortho-, meta- or para-position and having the formula:

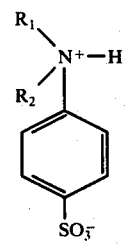

wherein $R_1$ and $R_2$ are selected from the group consisting of hydrogen, an alkyl, aryl, alkylaryl, aralkyl; hydrogen atoms in the benzene ring may be substituted by radicals of the group consisting of methyl alkyl, halide, and sulpho group; as well as a catalyst selected from the group of ammonium condensed compounds of the naphthalene series containing a sulpho group and having the formula:

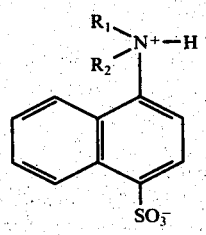

wherein $R_1$ and $R_2$ are selected from the group consisting of hydrogen, an alkyl, aryl, alkylaryl, aralkyl, and a reaction product of said ammonium compounds with formaldehyde, followed by isolation of the desired product.

14. A process as claimed in claim 13, wherein the reaction is performed in two successive temperature ranges, the first temperature range being from 70° to 130° C; the second temperature range being from 160° to 200° C.

15. A process as claimed in claim 13, wherein as the catalyst use is made of a compound selected from the group consisting of sulphanilic acid, methanilic acid, orthanilic acid, aniline-3,5-disulphonic acid, 2,5-dichloroaniline-4-sulphonic acid, 4-toluidine-3-sulphonic acid, monobenzylsulphanilic acid, dibenzylsulphanilic acid and 1-naphthylamine-4-sulphonic acid.

16. A process as claimed in claim 13, wherein as the catalyst use is made of a reaction product of formaldehyde with a compound selected from the group consisting of sulphanilic acid, sulphamic acid, methanilic acid, and 1-naphthylamine-4-sulphonic acid.

* * * * *